United States Patent
Raghavan et al.

(10) Patent No.: US 12,051,024 B2
(45) Date of Patent: Jul. 30, 2024

(54) AUTOMATED CONTROLLED-CASE STUDIES AND ROOT-CAUSE ANALYSIS FOR HOSPITAL QUALITY IMPROVEMENT

(71) Applicant: KONINKLIJKE PHILIPS N.V., Eindhoven (NL)

(72) Inventors: Ushanandini Raghavan, Lexington, MA (US); Daniel Robert Elgort, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 298 days.

(21) Appl. No.: 15/756,596

(22) PCT Filed: Aug. 25, 2016

(86) PCT No.: PCT/IB2016/055059
§ 371 (c)(1),
(2) Date: Mar. 1, 2018

(87) PCT Pub. No.: WO2017/037581
PCT Pub. Date: Mar. 9, 2017

(65) Prior Publication Data
US 2018/0181899 A1    Jun. 28, 2018

Related U.S. Application Data

(60) Provisional application No. 62/214,226, filed on Sep. 4, 2015.

(51) Int. Cl.
*G06Q 10/0639* (2023.01)
*G06Q 10/04* (2023.01)
(Continued)

(52) U.S. Cl.
CPC ....... *G06Q 10/06395* (2013.01); *G06Q 10/04* (2013.01); *G06Q 10/06* (2013.01);
(Continued)

(58) Field of Classification Search
CPC .. G06Q 10/06395; G06Q 10/04; G06Q 10/06; G06Q 50/22; G16H 40/20; G16H 10/60; G16H 50/30; G16H 50/70
(Continued)

(56) References Cited

U.S. PATENT DOCUMENTS 7,353,238 B1 *  4/2008  Gliklich ............... G16H 40/20
7,617,115 B2    11/2009  McNair
(Continued)

OTHER PUBLICATIONS

A predictive analytics approach to reducing 30-day avoidable readmissions among patients, Issac Shams, Healthcare Systems Engineering Group, Wayne State University, Detroit, MI 48201 (Year: 2015).*

(Continued)

*Primary Examiner* — Abdallah A El-Hage Hassan (57) ABSTRACT

A risk-adjusted assessment of a target facility's quality measures (e.g. mortality rate, length of stay, readmission rate, complications rate, etc.) is determined with respect to the quality measures of a broader population base. Patient cohorts are identified corresponding to particular ailments or treatments, and the target facility's risk-adjusted quality measures are determined for each cohort. When a particular quality measure for a target cohort indicates poor performance, factors that are determined to be relevant to the patients' outcomes are identified and used to create a control group of patients in the broader population who exhibit similar factors but had better outcomes than the patients of the target cohort. The care process (treatments, medications, interventions, etc.) that each of the target patients received is compared to the care process that each of the control patients received, to identify potential root-causes of the poorer performance.

3 Claims, 5 Drawing Sheets

(51) Int. Cl.
*G06Q 10/06* (2023.01)
*G16H 10/60* (2018.01)
*G16H 40/20* (2018.01)
*G16H 50/30* (2018.01)
*G16H 50/70* (2018.01)

(52) U.S. Cl.
CPC ............. *G16H 10/60* (2018.01); *G16H 40/20* (2018.01); *G16H 50/30* (2018.01); *G16H 50/70* (2018.01)

(58) Field of Classification Search
USPC ........................................................ 705/7.41
See application file for complete search history.

(56) References Cited

U.S. PATENT DOCUMENTS

| | | | |
|---|---|---|---|
| 8,620,690 B2 | 12/2013 | Hu et al. | |
| 8,762,169 B2 | 6/2014 | Mohlenbrock et al. | |
| 2005/0261941 A1* | 11/2005 | Scarlat | G16H 10/60 705/3 |
| 2007/0244724 A1 | 10/2007 | Pendergast et al. | |
| 2008/0154637 A1 | 6/2008 | Capelli et al. | |
| 2009/0119130 A1* | 5/2009 | Kimmel | G16H 15/00 705/3 |
| 2013/0262360 A1* | 10/2013 | Geleijnse | G16H 50/70 706/46 |
| 2013/0304499 A1* | 11/2013 | Rangadass | G06Q 10/063114 705/2 |
| 2014/0088990 A1* | 3/2014 | Nawana | G16H 50/70 705/2 |
| 2014/0236630 A1 | 8/2014 | Murata | |
| 2014/0244295 A1 | 8/2014 | Carroll et al. | |
| 2014/0324472 A1* | 10/2014 | Delaney | G16H 10/60 705/3 |
| 2015/0032467 A1* | 1/2015 | Rapp | G06Q 10/10 705/2 |
| 2015/0213223 A1* | 7/2015 | Amarasingham | G16H 50/30 705/2 |

OTHER PUBLICATIONS

Horwitz et al. "Hospital-wide (all-condition) 30-day risk-standardized readmission measure", Yale New Haven Health Services Corporation/Center for Outcomes Research & Evaluation, Retrieved Sep. 10, 2011: 2012.

Norén, G. Niklas, et al. "Temporal pattern discovery in longitudinal electronic patient records", Data Mining and Knowledge Discovery 20.3 (2010): 361-387.

M. Markatou, et al., "Case-based reasoning in comparative effectiveness research", IBM Journal of Research and Development, vol. 56, issue 5, 2012.

Fritsche, L., et al. "Recognition of critical situations from time series of laboratory results by case-based reasoning", Journal of the American Medical Informatics Association 9.5 (2002): 520-528.

Fisher, Elliott S., et al. "The implications of regional variations in Medicare spending. Part 1: the content, quality, and accessibility of care." Annals of internal medicine 138.4 (2003): 273-287.

* cited by examiner

| 402a | Mortality | Length of stay | Re-admission | Compli-cations | Volume |
|---|---|---|---|---|---|
| Defib implant with catheter | ⇧ ↑ | ⇩ ↑ | ⇧ ↑ | ⇧ ↓ | ▬▬▬▬▬ |
| Defib implant w/o catheter | ⇧ ↑ | ⇧ | | ↑ | ▬▬▬ |
| Perc proc w stent w/o MCC | ↑ | ⇧ | ⇧ ↓ | ↑ | ▬▬▬▬▬▬ |
| Perc proc w/o stent w/o MCC | ↓ | ⇩ | | ⇩ | ▬▬▬ |
| Defib implant w cath w MCC | ↓ | ↓ | ⇧ | ⇩ | ▬▬▬▬ |
| Defib implant w cath w/o MCC | ⇩ ↓ | | ⇧ ↑ | ⇩ | ▬▬ |
| Defib implant w/o cath w/o MCC | ⇩ ↑ | ⇧ | ⇩ ↑ | ↓ | ▬▬▬ |
| Defib implant w/o cath w MCC | ⇩ | ⇩ | | ⇩ ↓ | ▬▬▬ |
| Pacemaker w MCC | ⇩ | | ⇧ ↑ | ⇩ ↑ | ▬ |
| Pacemaker w/o MCC | ⇩ ↓ | ⇧ ↓ | | ↓ | ▬▬▬ |

AUTOMATED CONTROLLED-CASE STUDIES AND ROOT-CAUSE ANALYSIS FOR HOSPITAL QUALITY IMPROVEMENT

CROSS-REFERENCE TO PRIOR APPLICATIONS

This application is the U.S. National Phase application under 35 U.S.C. §371 of International Application No. PCT/IB2016/055059, filed on 25 Aug. 2016, which claims the benefit of U.S. Provisional Patent Application No. 62/214,226, filed on 4 Sep. 2015. These applications are hereby incorporated by reference herein.

FIELD OF THE INVENTION

This invention relates to the field of medical systems, and in particular to a system and method for providing a quality-improvement plan for a hospital based on analyses of performance and outcomes in a data-driven manner.

BACKGROUND OF THE INVENTION

Improving the quality of medical care and patient outcomes has been, and continues to be important to hospitals and care providers for altruistic reasons, and recent developments have made such improvements also important for economic reasons.

Figure 1:
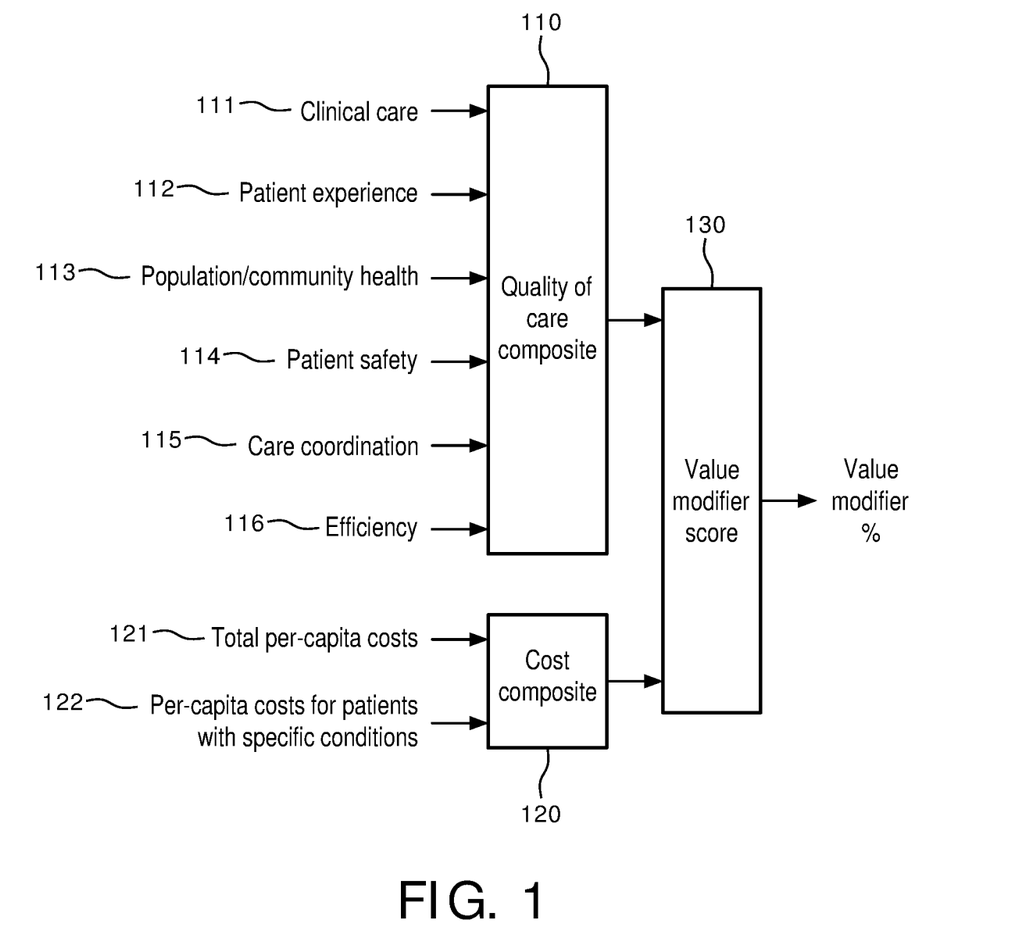
FIG. 1 illustrates the Value Modifier system that is administered by CMS.

The Centers for Medicare and Medicaid Services (CMS), as well as a number of medical insurance providers, have instituted or proposed programs that structure the reimbursement for services provided by medical practitioners and facilities based upon patient outcome, rather than the complexity of the provided service. FIG. 1 illustrates the CMS "Value Modifier" system for adjusting Medicare payments to a medical care provider or facility (collectively, 'facility') based on the facility's quality of care 110 and costs 120 of a prior year (e.g. in 2014, the facility's quality of care and costs in 2013 are used to determine the adjustment to Medicare payments to the facility in 2015).

As illustrated, CMS assesses the facility's performance in a number of categories 111-116 to determine a quality of care composite 110, and the facility's costs 121-122 to determine a cost composite 120. These composites 110, 120 are used to determine a value modifier score 130, from which a value modifier percentage is determined (typically +/− a few percent). Thereafter, this percentage is added or subtracted from the Medicare reimbursements from CMS to the facility.

Figure 2:
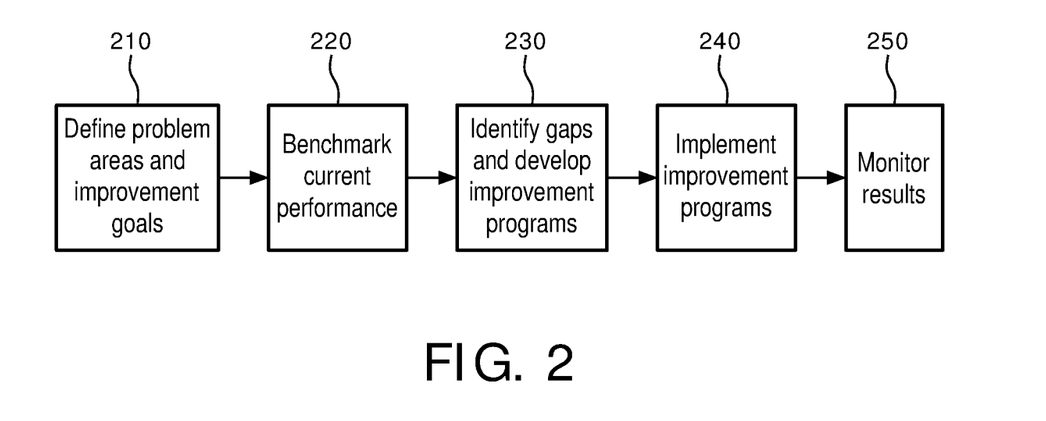
FIG. 2 illustrates an example performance and quality improvement program.

A facility may institute a quality improvement program such as illustrated in FIG. 2 to assure that problem areas are addressed. At 210, the problem areas are identified, and goals are set to improve performance and quality of care in these areas. For each problem area, the current performance is benchmarked at 220, to facilitate a determination of whether the performance is improving. To improve performance, gaps or deficiencies in the problem area are identified, and improvement programs that address these deficiencies are developed, at 230, and implemented, at 240. The results of the improvement programs are monitored at 250 and compared to the original benchmark to determine whether the improvement program is working effectively.

Such programs have been made feasible or practical due to the availability of electronic medical records (EMR), so that expert opinions and decisions can be reached based on a significant amount of quantifiable empirical evidence. However, even though it is becoming increasingly common for healthcare facilities to emphasize the quantification of quality and performance, available methods and tools do not adequately support the identification of underlying causes and drivers of quality/performance (both good and bad) in an automated or data-driven manner.

In many cases, the root-cause of an identified problem is directly apparent. For example, a measure of performance may include the percentage of patients for whom a particular test was administered after the patient was prescribed a particular medication. If this measure indicates a problem, the solution (assure that the test is administered) is apparent, because the cause of the problem (neglecting to administer the test) is apparent.

In other cases, the root-cause of an identified problem is not directly deducible from the measure of performance. For example, a measure of performance may include the percentage of patients that are readmitted for the same malady or complications thereof. If this measure indicates a problem, the solution is not apparent because the root cause of these readmissions is unknown.

Additionally, identifying problem areas is often not a simple process. The problem area may, for example, be ailment-specific. The outcome of a patient experiencing a first ailment may be highly dependent upon the medication prescribed, whereas the outcome of a patient experiencing a second ailment may be substantially independent of the prescribed medicine, but highly dependent upon the particular tests administered to distinguish this ailment from others. On average, a quality measure for a target facility may appear to be acceptable over all ailments, and not identified as a problem area; but an abnormal quality measure for the first ailment may be masked by a higher quality measure for the second ailment.

Even when focused on a specific ailment, the identification of a problem area is hampered by the lack of knowing what constitutes 'normal' performance, and what constitutes 'abnormal' performance. A mortality statistic may be easy to calculate, for example, but the interpretation of this statistic to determine if this statistic indicates a problem area is, in most situations, subjective.

SUMMARY OF THE INVENTION

It would be advantageous to provide a method and system that enables a medical facility to identify the root causes and drivers of performance and quality. It would also be advantageous to enable a determination of specific areas needing improvement within a given facility, and providing recommendations for improvement based on these root causes and drivers of performance and quality.

To better address one or more of these concerns, in an embodiment of this invention, a risk-adjusted assessment of a target facility's quality measures (e.g. length of stay, mortality, readmissions, complications, infections, etc.) with respect to the quality measures of a broader population base is determined to identify poor performance at the target facility. Individual patient cohorts are identified corresponding to particular ailments or treatments, and the target facility's quality measures are determined for each cohort. When a particular quality measure for a target cohort indicates poor performance, factors that are determined to be relevant to the patients' outcomes are identified and used to create a control group of patients in the broader population who exhibit similar factors and had better outcomes than the patients of the target cohort. The care process (treatments, medications, interventions, etc.) that each of the target patients received is compared to the care process that each of the control patients received, to identify potential root-causes of the poorer performance. Recommendations for correcting the root-cause(s) of the differences in services are provided, with the expectation that such correcting will result in an improvement in the given quality measure at the target facility.

In an embodiment of this invention, the performance analysis system may: determine, for a target patient group and a target ailment, whether a target medical facility's outcomes are abnormal compared to patient outcomes at a plurality of other medical facilities; determine relevant patient factors from a plurality of patient factors that characterize the target patient group; select, based on the relevant patient factors, one or more other patients that experienced better outcomes than the target patient group; identify differences in treatment between the one or more other patients and the target patient group to determine one or more root-causes of the abnormal outcomes; and provide one or more recommendations for improved performance to the medical facility, based on the identified differences in treatment.

The performance analysis system may also determine a relative impact of potential performance improvements at the medical facility with regard to the target patient group, based on a relative volume of the target patient group.

The performance analysis system may also create a predictive model that is configured to receive patient characteristics for each target patient of the target patient group and provide a predicted outcome for each target patient based on the patient outcomes at the plurality of other medical facilities, and may determine whether the facility's outcomes are abnormal based on the predicted outcome for each patient of the target patient group.

The performance analysis system may also determine whether the medical facilities outcomes are abnormal for each of a plurality of quality measures, including, for example, mortality rate, length of stay, readmission rate, complication rate, and infection rate.

The performance analysis system may also identify a similarity factor for each patient with the target ailment in the plurality of other facilities compared to the target patients; and to select the one or more other patients based on the similarity factors.

The performance analysis system may also provide a presentation of the facility's outcomes compared to the outcomes at the plurality of other medical facilities.

BRIEF DESCRIPTION OF THE DRAWINGS

The invention is explained in further detail, and by way of example, with reference to the accompanying drawings wherein.

Throughout the drawings, the same reference numerals indicate similar or corresponding features or functions. The drawings are included for illustrative purposes and are not intended to limit the scope of the invention.

DETAILED DESCRIPTION

In the following description, for purposes of explanation rather than limitation, specific details are set forth such as the particular architecture, interfaces, techniques, etc., in order to provide a thorough understanding of the concepts of the invention. However, it will be apparent to those skilled in the art that the present invention may be practiced in other embodiments, which depart from these specific details. In like manner, the text of this description is directed to the example embodiments as illustrated in the Figures, and is not intended to limit the claimed invention beyond the limits expressly included in the claims. For purposes of simplicity and clarity, detailed descriptions of well-known devices, circuits, and methods are omitted so as not to obscure the description of the present invention with unnecessary detail.

In the quality improvement process of FIG. 2, a first step is the identification of problem areas in the care process of a facility (hereinafter, the 'target facility'). This is often a complex task because an identification of a problem area is often a subjective assessment, with no baseline for comparison. As noted above, many statistics are easy to calculate, such as mortality rates, average length of stay, and so on, but the interpretation of these results to determine whether a problem exits is not straightforward. For example, a facility may experience a particular mortality rate that seems 'high', but this facility's patients may be predominantly bed-ridden geriatric patients, as contrast to another facility whose patients are predominantly young or middle-aged. Similarly, an oncologist may experience a higher mortality rate than a pediatrician.

To properly assess the outcome of a patient of a particular facility, this patient's outcome needs to be "risk-adjusted" by comparing this patient's outcome to the "expected outcome" of a person with the particular characteristics of this patient experiencing the same ailment. That is, for example, the expected likelihood of complications after surgery of a patient with diabetes will generally be higher than that of a patient without diabetes, and the determination of whether a problem exists with regard to complications after surgery needs to take into consideration whether or not each patient was diabetic before the surgery.

Fortunately, with the increasing availability of electronic medical records (EMR) that can be shared among facilities provides an opportunity for a risk-adjusted assessment of the target facility's performance relative to a large population of facilities by comparing each patient's outcome with the "expected outcome" for this patient. If a significant number of patients experience an outcome that was worse than the expected outcome, a problem in the facility's service of care is likely to exist.

Figure 3:
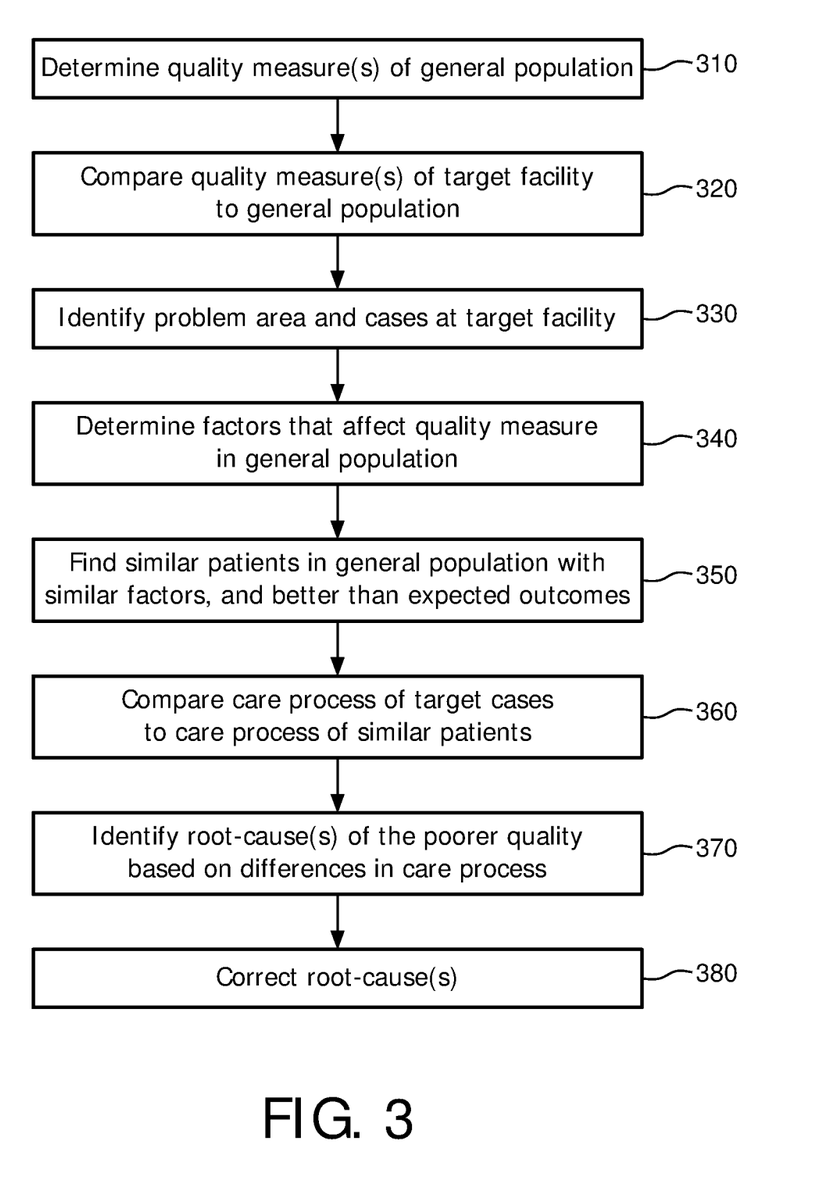
FIG. 3 illustrates an example flow diagram of a method for identifying and correcting the root-cause(s) of poor quality of care in accordance with aspects of this invention.

In the example process flow of FIG. 3, a first step 310 is the identification of quality measures, and a determination of the achieved quality, as measured by the quality measure, across the general population of facilities. A number of outcome-based quality measures may be used, including, for example, mortality, length of stay, readmissions, complications, infections, and so on. One of skill in the art will recognize that in addition to such objective measures, other, more subjective, measures of quality may be identified, such as patient feedback and others.

The quality measure may be determined for different categories of patient diagnoses (e.g. cardiovascular, pulmonary, neurologic, etc.), or a finer resolution may be obtained by categorizing the patients into smaller groups, or cohorts with similar diagnoses or treatment regiments. For example, within the group of patients who have been treated for cardiovascular ailments, separate cohorts may be defined based on the procedure used to treat each patient, including, for example, patients who received defibrillation implants and patients who received pacemakers. Within these groups, further partitioning may be defined based on whether other treatments (e.g. stents, catheters, etc.) were administered, or whether the patient exhibited particular characteristics (e.g. diabetes, COPD, etc.).

For each defined cohort, the records of the patients within this cohort are accessed to extract patient characteristics, such as age, sex, weight, race, insurance type, primary diagnosis, secondary diagnoses, vital signs, and test results, typically obtained at or near the time of admission. Preferably, the cohort includes a wide collection of characteristics obtained from a wide range of peer facilities, such as a regional database of electronic medical records. The outcome for each patient for each quality measure (e.g. mortality, length of stay, readmission, complications, etc.) is also extracted/calculated.

From this extracted data, a model may be created to determine the relationship(s) between the patient characteristics (inputs to the model) and the resultant outcome (output of the model). Any number of known techniques may be used to create such a model, including learning systems that may use Neural Networks, Bayesian Networks, Hidden Markov Models, Decision Trees, Ensembles (Random Forest), Linear or Logistic Recession, and so on. This model may subsequently be used to predict an outcome based on each particular patient's characteristics.

At 320, the risk-adjusted score for each quality measure at the target facility is determined, based on the records of the patients of the target facility. To calculate the risk-adjusted score for a patient cohort, let $O_{ij}$ represent the observed outcome for patient i in cohort j in a given hospital and let Eij be the predicted outcome of patient i obtained from the model, based on this patient's characteristics that are input to the model. The ratio $$\frac{\Sigma_i O_{ij}}{\Sigma_i E_{ij}}$$

is the risk adjusted performance score for the patient cohort. In the case where the outcomes are a continuous variable (such as length of stay) as opposed to categorical (such as mortality), the ratio for an individual patient $$\frac{O_i}{E_i}$$

may also be calculated.

For categorical outcomes, a binary 0, 1 value is used for the absence or presence of the outcome, respectively. That is, if the patient experienced complications, the observed outcome for the quality measure of complications will be 1. Accordingly, if the ratio $$\frac{\Sigma_i O_{ij}}{\Sigma_i E_{ij}}$$

is greater than 1, the target facility has experienced a higher-than-average occurrence of the quality mesure. For continuous variable outcomes, the ratio $$\frac{\Sigma_i O_{ij}}{\Sigma_i E_{ij}}$$

will indicate whether the average observed value is higher or lower than the average expected value. For consistency, the quality measures are typically defined such that a lower score is preferred (e.g. "mortality rate", "length of stay"); however, one of skill in the art will recognize that differently defined quality measures (e.g. "survival rate") may imply that a higher score is preferred. As used in the examples herein, a lower value for each quality measure is assumed to be preferred.

Figure 4:
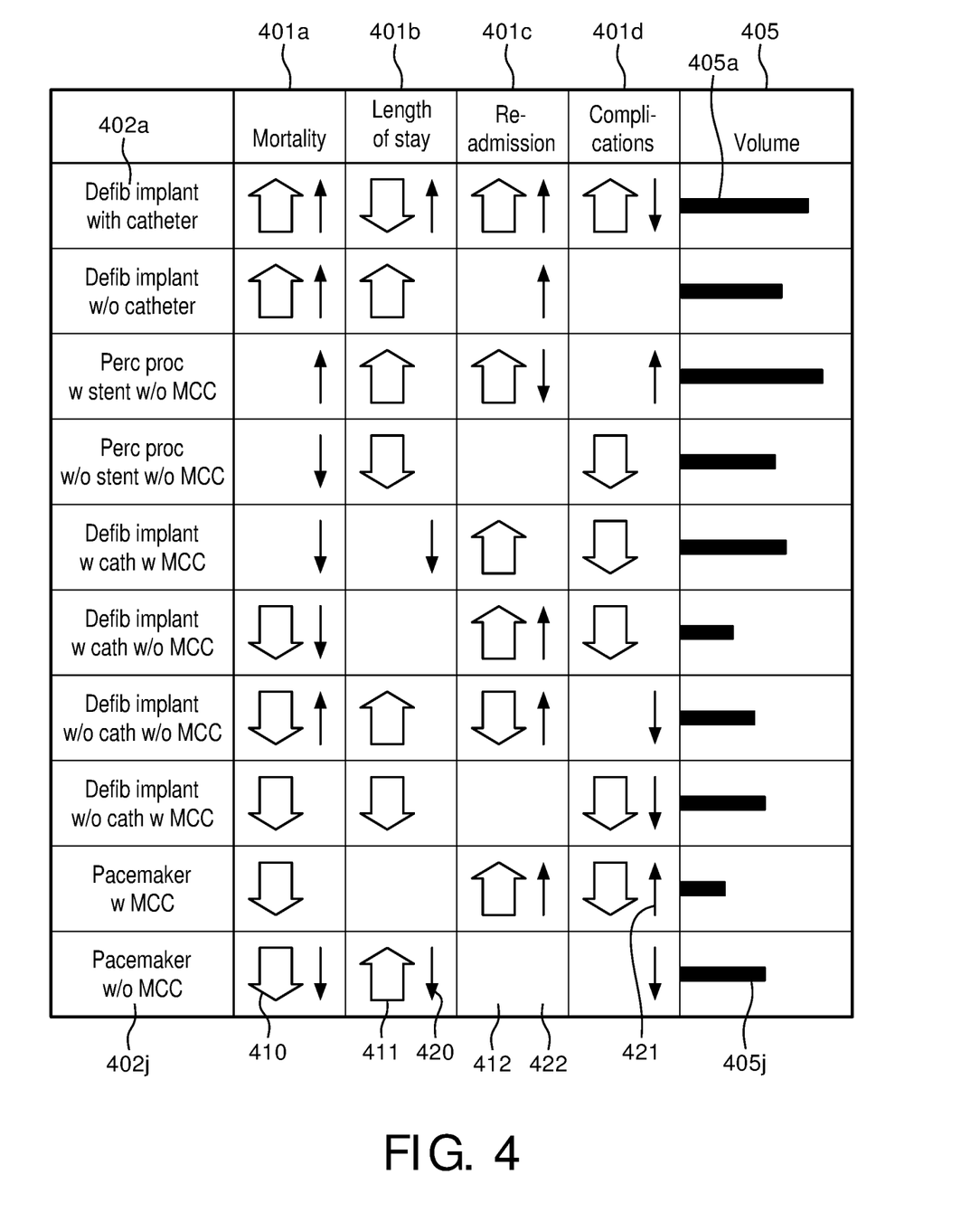
FIG. 4 illustrates an example presentation of a facility's quality of care as compared to the quality of care of a broader population of facilities.

FIG. 4 illustrates an example presentation of the results of a risk-adjusted assessment of a facility's performance as measured by mortality rate 401a, length of stay 401b, re-admission rate 401c, and complications rate 401d. These performance measures are determined for each of ten patient cohorts 402a ... 402j.

In this presentation, a broad "down" arrow 410 is used to indicate a quality measure that is below the average (better performance); a broad "up" arrow 411 indicates a quality measure that is above the average (poorer performance); and the absence 412 of a broad arrow indicates on-par performance. In an alternative presentation, different colors may be used to indicate the comparative performance, such as green for above-average, red for below-average, and white or yellow for on-par performance. In like manner, the size of the broad arrow, or the intensity of the color, may be dependent upon the magnitude of ratio $$\frac{\Sigma_i O_{ij}}{\Sigma_i E_{ij}},$$

so that the 'severity' of the problem, if any, may be indicated directly.

In an example embodiment, a 'threshold ratio' is used for distinguishing these levels of performance. For example, instead of using a ratio $$\frac{\Sigma_i O_{ij}}{\Sigma_i E_{ij}}$$

value of 1.0 as the criteria for determining whether a target facility's quality measure is above or below average, a value of 1.2 may be used to define a quality measure that is above average (poor performance), and a value of 0.8 used to define a quality measure that is below average (better performance). Values of the ratio $$\frac{\Sigma_i O_{ij}}{\Sigma_i E_{ij}}$$

between 0.8 and 1.2 in this example would be defined as on-par performance. One of skill in the art will recognize that these threshold values may be defined differently for each quality measure, depending upon the variance of the quality measure and other factors.

In the example presentation of FIG. 4, the cohort 402j of patients at the target facility who received a pacemaker without MCC (Major Complications and Comorbidities) exhibited lower than average mortality rate 410 than the general population of patients who received a pacemaker without MCC, and the average length of stay was longer than the average length of stay of the general population of patients who received a pacemaker without MCC. The readmission rate and complications rate for this facility was on par with the general population of patients who received a pacemaker without MCC.

Optionally, illustrated in FIG. 4 are narrow arrows 420, 421 that indicate how the performance at the target facility has been changing over time. The change may be measured based on a benchmark measure, a running average, and so on. In this example, although the cohort 402j exhibited a longer length of stay 411 than expected, based on the model, the length of stay has been decreasing 420, indicating an improvement in this measure.

Also illustrated in FIG. 4 is the number of patients (volume) 405 in each cohort 402a . . . 402j. This volume 405a . . . 405j may be used to prioritize the problem areas that need to be addressed, along with the severity of the problem (magnitude of the ratio $$\frac{\Sigma_i\, O_{ij}}{\Sigma_i\, E_{ij}} \Bigg),$$

and other factors. That is, for example, a problem may be severe, but may only affect a small proportion of patients. Addressing this problem may be given a lower priority than a problem of the same severity that affects a large proportion of patients, and perhaps a lower priority than a problem of lesser severity that affects a large proportion of patients.

At 330, a particular problem area for a given cohort is identified, along with the patients of this cohort. For example, the higher-than-expected readmittance rate 401c (the target quality measure) of cohort 401a (the target cohort) may be selected as a first problem to be addressed. A solution or remedy to this problem (other than "reduce readmittance rate") is not directly apparent, but the availability of the patient records of the general population, including the specific care that each patient received, provides the potential of comparing the care provided by the target facility to the care provided by the general population, particularly in the cases where better outcomes were achieved in the general population. To provide such a comparison, the care provided to 'similar' patients in the general population who experienced better outcomes needs to be determined.

In the determination of whether one patient is similar to a target patient, the question of "similar in what regard?" must be answered. In an example embodiment of this invention, the patient characteristics that appear to have had the largest impact on the outcome are identified, and these characteristics (relevant factors) are used to define similarity with regard to this particular problem area.

At 340, the records of patients in the general population of the same cohort of the target facility are used to identify which particular patient characteristics (factors) have the greatest effect on the determined value of the quality measure. Any number of techniques may be used to determine which factors are most relevant to the outcome.

Independent of the model, a regression analysis may be performed for each characteristic to determine whether there is a strong correlation between the particular characteristic and the outcome. Other statistical techniques may be used, including for example ANOVA (Analysis of Variance) and others.

Alternatively, or additionally, the records of the patients in the general population may be used as input to the model, but with random permutations of the value of each characteristic. The magnitude of the variance of the outcomes with these random permutations provides an indication of the characteristics that have the most impact on the outcome.

Other techniques may be applied as well. For example, if it is assumed that particular combinations of characteristics have a significant effect on the outcome, that may not be apparent when assessing each characteristic independently, or if some characteristics are 'redundant', such that including either characteristic has the same effect on the outcome, multi-variate analysis techniques may be applied. For example, a genetic algorithm may be used, wherein different combinations of inputs are iteratively tested for their effectiveness in predicting the correct outcome, and the most effective input set of relevant factors is identified.

Having identified the factors that have the largest impact on the outcome, patients in the general population of the same cohort as the target cohort are assessed to identify 'control' patients that are 'similar' to the patients in the target cohort, but with better outcomes.

Similarity between factors may be determined in any number of ways, the most common being a representation of the factors as a vector, then determining the distance between patients using Euclidean distance, Mahalanobis distance, Manhattan distance, and others. Patients in the cohort of the population that had a better outcome and are within a threshold distance from patients in the target cohort are selected as being similar to the patients in the target cohort.

At 360, the care process of the patients of the target cohort is compared to the care process that the patients in the general population who had positive outcomes. The comparison may include a variety of metrics, including, for example: Diagnostic Exams; Medications Administered; Procedures Administered; Tests Performed; Physician Qualifications; and others. In addition to these explicit care metrics, other considerations may also be included, such as whether the patient was in a private room, the patient to nurse ratio, the time between nurse visits, and so on.

Of particular note, as compared to the quality measures 401a-401d, the root-cause metrics each directly identify a solution or remedy. If a particular diagnostic exam was regularly performed for the control patients, but not for the patients in the target cohort, for example, the solution would appear to be to perform this diagnostic exam regularly for future patients in this cohort. In like manner, if the control patients predominantly had private rooms, and the patients in the target cohort predominantly had semi-private rooms, the solution would appear to be to add more private rooms for future patients in this cohort.

When a root-cause is identified for which the root-cause metric for the control patients differed significantly from the root-cause metric of the patients of the target cohort, this root-cause is reported, at 370, and a solution that addresses this root cause is identified and implemented to correct the root-cause of the identified problem area, at 380, to indirectly improve the target quality measure being addressed for the target cohort.

Each quality measure that indicates a problem for a given cohort at the target facility, based on a risk-adjusted assessment compared to the same cohort of the general population, may subsequently be analyzed as detailed above to identify the root cause(s) of the problem that negatively affected the quality measure.

Figure 5:
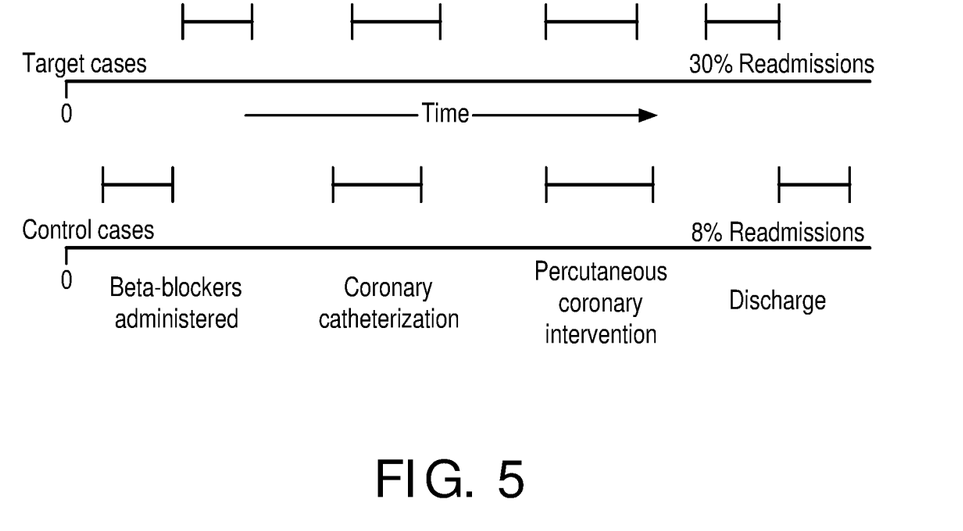
FIG. 5 illustrates an example presentation of a comparison between a facility's care process and the care process provided to similar patients that had better outcomes at other facilities.

FIG. 5 illustrates an example presentation of a variety of root-cause metrics as applied over time for the example target cohort and corresponding control cases. These metrics include the time since admission of: administering beta-blockers, a coronary catheterization procedure, a percutaneous coronary intervention, and patient discharge. These times for each of the control cases from the general population and the target cases of the target facility is illustrated as a function of time in FIG. 5.

As can be seen, the time of administering beta-blockers indicates a significant difference between the target cases and the control cases that had a better outcome with respect to readmissions. This evidence would suggest that the target facility should administer beta-blockers to future patients in the target cohort to reduce the likelihood of these patients being readmitted for the same or related ailments.

Additionally, the patients in the target cohort were discharged sooner than the control patients of the general population. Although this results in a shorter-than-average length of stay 401*b* for this target cohort 402*a*, the effect on the readmission rate may suggest that more time is needed to monitor the patient after a percutaneous coronary intervention, before discharge.

Figure 6:
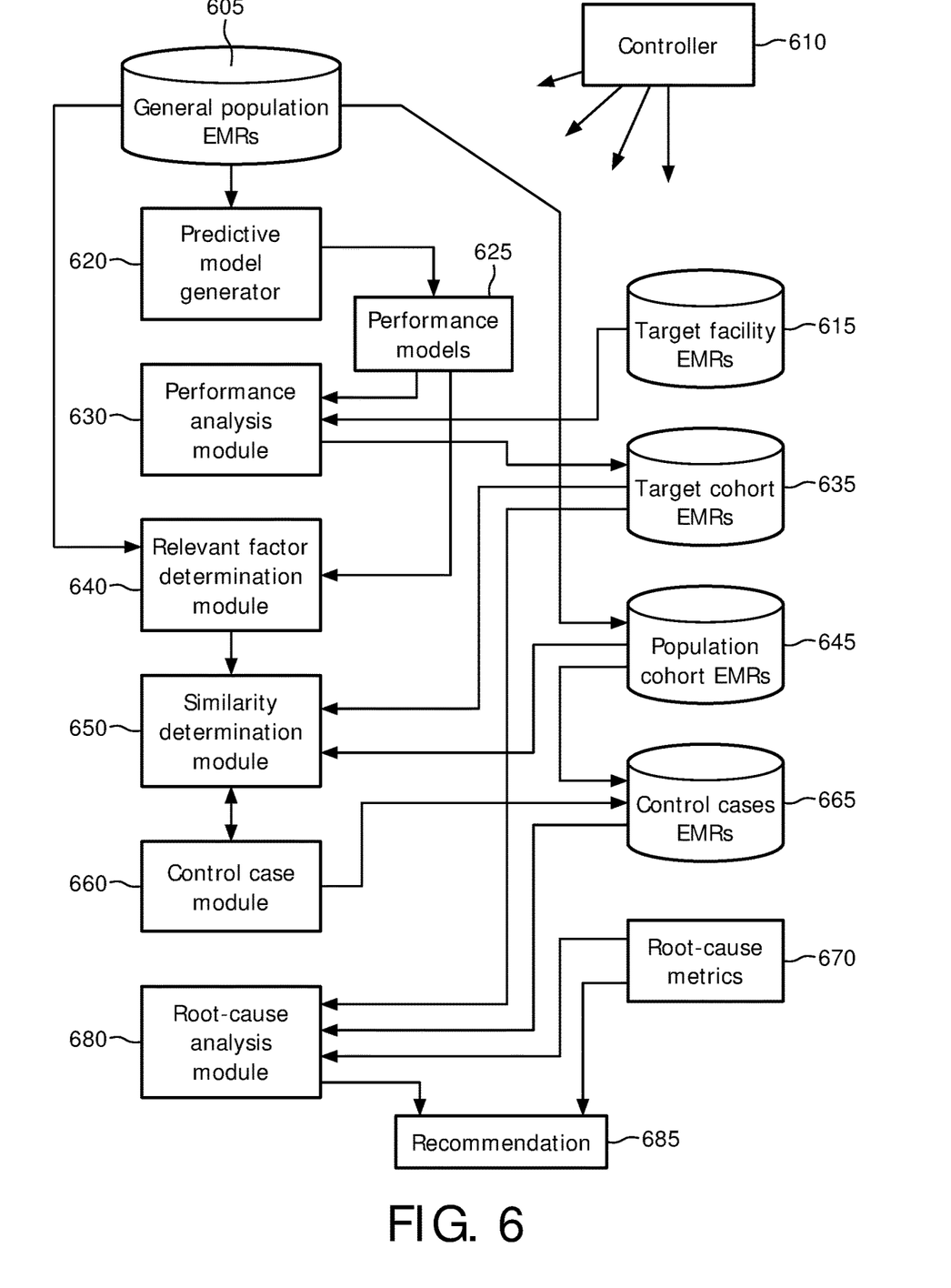
FIG. 6 illustrates an example block diagram of a quality improvement system in accordance with aspects of this invention.

FIG. 6 illustrates an example block diagram of a medical performance analysis system 600 in accordance with aspects of this invention. The system 600 includes a controller 610 that is configured to manage the subsequently described operations and processes.

A prediction model generator 620 is configured to create performance models based on the electronic medical records 605 of patients of a general population, such as may be included in a regional medical database, or a collection of databases at multiple facilities. A plurality of performance models may be created, corresponding to a matrix of quality measures and patient cohorts. That is, for each identified patient cohort, the records of the patients within the cohort are assessed to identify the characteristics of each patient that received treatment, and the outcomes of the treatment with respect to each of a plurality of defined quality measures, such as mortality, length of stay, readmissions, complications, infections, and so on. These characteristics and outcomes are used to create a performance model 625 for each quality measure for each cohort, using, for example, any of a variety of learning systems, as detailed above.

A performance analysis module 630 is configured to assess the performance of a target facility with regard to each cohort's performance for each of the aforementioned quality measures. This assessment is performed in a risk-adjusted manner by comparing the outcomes for each patient in a given cohort at the target facility to a predicted outcome for the patient based on the patient's characteristics applied as input to the corresponding performance model 625 for this cohort.

Based on these assessed risk-adjusted performances for each cohort with regard to each quality measure, one or more problem areas may be identified. One or more of these problem areas may be selected to be addressed to remedy the problem. The selection of problem areas to be addressed may be dependent upon the expected benefit to be derived from the remedy and the expected cost of implementing the remedy. The expected benefit may be dependent upon the number (volume) of patients in the cohort as well as the magnitude of the difference between the outcomes of the patients in the cohort in the target facility and the outcomes of the patients in the same cohort in the general population.

For the selected problem area (cohort, quality measure) to be addressed, the medical records 635 of the patients in the cohort are identified, from which the medical records 645 of the patients in the same cohort in the general population may also be identified. The patients 645 are further filtered by identifying patients within this cohort of the general population that are similar to the patients 635 within the target cohort with respect to factors that are considered to be relevant to the quality measure being addressed.

A relevant factor determination module 640 is configured to determine the factors that are relevant to the quality measure being addressed, using any of the techniques detailed above, including regression analysis, analysis of variance, permutations of values applied to the performance model, genetic algorithms, and so on. These relevant factors are used to identify patients in the cohort of the general population that are similar to the patients in the target cohort with regard to these relevant factors, using the similarity determination module 650. As noted above, any number of known techniques may be used to identify patients with similar relevant factors, most commonly based on a factors vector and the distance between the factors vector of the target patient and the patient in the general population. [* To be enhanced upon receipt of info requested above *]

A control case module 660 assesses the determined similarities and selects the control cases of patients 665 from the cohort of the general population who have had a positive outcome and have the most similarity to patients in the target cohort [who experienced an adverse outcome?] [* To be enhanced upon receipt of info requested above *]

A root-cause analysis module 680 obtains a set of root-cause metrics (measures of potential root-causes) 670 and compares the root-cause metrics determined from the patient records 635 in the target cohort to the root-cause metrics determined from the patient records 665 in the control cases. The set of root-cause metrics may be any of a variety of aspects of the care processes at the target facility and in the general population. Some of the root-cause metrics may be specific to particular cohorts, such as the administration of beta-blockers for certain cardiovascular cohorts; while some of the root-cause metrics may be applicable to all cohorts, such as obtaining the patient's vital signs. The metric may be a single time-invariant value, while most metrics will include a time of occurrence associated with each metric.

The root-cause analysis module determines whether a significant difference exists between the root-cause metrics of the target cohort and the control cases. If a significant difference is detected, it is reported with a recommendation 685 that this root-cause metric be considered as a potential cause of the identified problem area (poor performance within the target cohort with regard to the target quality measure).

Each root-cause metric that is found to differ between the target cohort of patients with a poor outcome and the control cases of similar patients with positive outcomes is similarly reported in the recommendation 685. Optionally, this recommendation 685 may prioritize the identified root-cause metrics based on the volume of the target cohort and/or based on the severity of the difference in the quality measure, as detailed above.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein a predefined set of patient characteristics are used as the relevant factors for determining similarity. Such an approach, however, may be less efficient, and some meaningful characteristics may be masked by characteristics in the predefined set that do not directly impact the outcome.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for generating one or more recommendations for improved performance to a medical facility using a medical performance analysis system, comprising:
    generating a predictive model based on electronic medical records of patients of a general population, the electronic medical records received from a plurality of other medical facilities, the predictive model configured to receive patient characteristics for each target patient of a target patient group and provide a predicted outcome for each target patient;
    determining, for the target patient group and a target ailment, whether a medical facility's outcomes are abnormal based on a risk-adjusted score for each of a plurality of quality measures compared to patient outcomes at a plurality of other medical facilities, wherein the determination is based on the performance model and the predicted outcome for each patient of the target patient group, and wherein the plurality of quality measures includes mortality rate, length of stay, complication rate, and infection rate;
    determining relevant patient factors from a plurality of patient factors that characterize the target patient group;
    selecting, based on the relevant patient factors, one or more other patients that experienced better outcomes than the target patient group;
    identifying one or more differences in treatment between the one or more other patients and the target patient group;
    generating one or more recommendations for improved performance by the medical facility based on the identified differences in treatment, wherein the recommendation comprises a display of a plurality of quality measures for the medical facility, wherein the quality measures comprise an indication of the medical facility's performance relative to the performance of the plurality of medical facilities, and further wherein the provided one or more recommendations for improved performance comprises a recommendation to administer a beta blocker;
    providing, via the display, the one or more recommendations for improved performance, comprising optionally providing a presentation of the medical facility's outcomes compared to the outcomes at the plurality of other medical facilities; and
    administering, by one or more clinicians of the medical facility, the provided one or more recommendations for improved performance, comprising administrating, by one or more clinicians of the medical facility, a beta blocker to one or more target patients of the target patient group.

2. The method of claim 1, wherein identifying one or more differences in treatment between the one or more other patients and the target patient group comprises determining a relative impact of potential performance improvements at the medical facility with regard to the target patient group, based on a relative volume of the target patient group.

3. The method of claim 1, further comprising identifying a similarity factor for each patient with the target ailment in the plurality of other facilities compared to the target patients, wherein said selecting step further comprises selecting one or more other patients based on the identified similarity factors.

* * * * *